(12) United States Patent
Gore et al.

(10) Patent No.: US 9,616,017 B2
(45) Date of Patent: Apr. 11, 2017

(54) TWO PART FORMULATION SYSTEM FOR OPHTHALMIC DELIVERY

(71) Applicant: Allergan, Inc., Irvine, CA (US)

(72) Inventors: Anuradha V. Gore, Aliso Viejo, CA (US); Sai Shankar, Irvine, CA (US); Sukhon Likitlersuang, Irvine, CA (US); Chetan P. Pujara, Irvine, CA (US); Sesha Neervannan, Irvine, CA (US)

(73) Assignee: Allergan, Inc., Irvine, CA (US)

(*) Notice: Subject to any disclaimer, the term of this patent is extended or adjusted under 35 U.S.C. 154(b) by 0 days.

(21) Appl. No.: 15/135,925

(22) Filed: Apr. 22, 2016

(65) Prior Publication Data

US 2016/0235666 A1    Aug. 18, 2016

Related U.S. Application Data

(63) Continuation of application No. 13/557,611, filed on Jul. 25, 2012, now abandoned.

(60) Provisional application No. 61/511,753, filed on Jul. 26, 2011.

(51) Int. Cl.

| | | |
|---|---|---|
| *A61K 31/568* | (2006.01) |
| *A61K 38/13* | (2006.01) |
| *A61K 31/416* | (2006.01) |
| *A61K 31/4025* | (2006.01) |
| *A61P 27/02* | (2006.01) |
| *A61K 9/00* | (2006.01) |
| *A61K 47/34* | (2017.01) |
| *A61K 9/08* | (2006.01) |
| *A61K 31/417* | (2006.01) |
| *A61K 31/559* | (2006.01) |

(52) U.S. Cl.
CPC ............ *A61K 9/0048* (2013.01); *A61K 9/08* (2013.01); *A61K 31/417* (2013.01); *A61K 31/559* (2013.01); *A61K 31/568* (2013.01); *A61K 38/13* (2013.01); *A61K 47/34* (2013.01)

(58) Field of Classification Search
None
See application file for complete search history.

(56) References Cited

U.S. PATENT DOCUMENTS

| | | |
|---|---|---|
| 5,409,904 A | 4/1995 | Hecht et al. |
| 5,474,979 A | 12/1995 | Ding et al. |
| 6,335,022 B1 | 1/2002 | Simonnet et al. |
| 7,458,741 B2 | 12/2008 | Detwiler et al. |
| 2006/0257388 A1 | 11/2006 | Knowles |
| 2008/0004310 A1 | 1/2008 | Kelley, II |
| 2008/0095754 A1 | 4/2008 | Burke et al. |
| 2009/0092665 A1 | 4/2009 | Mitra et al. |
| 2010/0210681 A1 | 8/2010 | Bauer et al. |

FOREIGN PATENT DOCUMENTS

| | | |
|---|---|---|
| CN | 1185953 A | 7/1998 |
| CN | 102028697 A | 4/2011 |
| WO | 9841208 | 9/1998 |
| WO | WO01-019364 | 3/2001 |
| WO | 2009046967 A1 | 4/2009 |
| WO | 2009088570 A1 | 7/2009 |
| WO | WO2009040547 A3 | 9/2009 |

OTHER PUBLICATIONS

International Search Report and Written Opinion mailed on Jan. 2, 2013 for PCT/US12/48263 filed Jul. 26, 2012 in the name of Allergen, Inc.
Lallemand, F. et al, Cyclosporine a Delivery to the Eye: A Pharmaceutical Challenge, European Journal of Pharmaceutics and Biopharmaceutics, 2003, 307-318, 56.
Wenger, Robert A., Synthesis of Cyclosporine. Total Syntheses of 'Cyclosporin A' and 'Cyclosporin H', Two Fungal Metabolites Isolated from teh Species Tolypocladium Inflatum GAMS, Hevetica Chimica Acta, 1984, 502-525, vol. 67m Issue 2, No. 61.

*Primary Examiner* — Julie Ha
*Assistant Examiner* — Kristina M Hellman
(74) *Attorney, Agent, or Firm* — Laura L. Wine

(57) ABSTRACT

Ophthalmic products and related methods are described herein. These methods include a stabilizing composition comprising a therapeutically active agent which is separated from a liquid vehicle composition by a barrier. The barrier may be removed to allow the two compositions to mix to provide an ophthalmically acceptable liquid comprising the therapeutically active agent.

20 Claims, No Drawings

TWO PART FORMULATION SYSTEM FOR OPHTHALMIC DELIVERY

CROSS REFERENCE TO RELATED APPLICATION

This application is a continuation of U.S. patent application Ser. No. 13/557,611, filed on Jul. 25, 2012, which claims the benefit of U.S. provisional application Ser. No. 61/511,753, filed on Jul. 26, 2011, the entirety of both applications are hereby incorporated by reference.

FIELD

Embodiments include ophthalmic, otic and intranasal products and methods.

BACKGROUND OF THE INVENTION

For labile therapeutically active agents, traditional formulation development would include use of stabilizers and/or selection of pH range to optimize stability of the therapeutically active agents. However, high concentrations of stabilizers or selection of product pH that is outside physiological range may lead to safety and tolerability concerns for the product.

SUMMARY OF THE INVENTION

Some pharmaceutical products intended for ophthalmic, otic and intranasal delivery may be stabilized by making an ophthalmically acceptable liquid by reconstitution prior to dose delivery. This may be an advantage for chemically labile therapeutically active agents which may have a limited shelf life in a formulation suitable for ophthalmic delivery due to their rapid degradation rates.

Some embodiments include an ophthalmic pharmaceutical product comprising: a stabilizing composition comprising a therapeutically active agent; a liquid vehicle composition; a removable barrier; wherein the barrier is configured to prevent contact between the stabilizing composition and the liquid vehicle composition; and wherein the product is configured to allow removal of the barrier; wherein the product is configured so that removal of the barrier allows mixing of the stabilizing composition and the vehicle composition to provide a sterile ophthalmically acceptable liquid; wherein the ophthalmically acceptable liquid comprises a therapeutic amount of the therapeutically active agent.

Some embodiments include a method of stabilizing a therapeutically active agent for use in an ophthalmically acceptable liquid comprising: providing a stabilizing system comprising: a stabilizing composition comprising the therapeutically active agent; a vehicle composition comprising at least one of: a solubilizer, a surfactant, an osmolality agent, a buffer, and a preservative; and a removable barrier separating the stabilizing composition from the vehicle composition; wherein the system is configured so that removal of the barrier allows mixing between the stabilizing system and the vehicle to provide a sterile ophthalmically acceptable liquid; and wherein the ophthalmically acceptable liquid comprises about 0.0001% to about 5% therapeutically active agent by weight.

DETAILED DESCRIPTION OF THE INVENTION

Some embodiments may include a two part formulation product, which can be reconstituted by mixing the two parts. In this system, a stabilizing composition contains a therapeutically active agent in a formulation matrix that may improve the stability or shelf-life of the therapeutically active agent in the formulation matrix. The product also comprises a liquid vehicle composition. The stabilizing composition is separated from the liquid vehicle composition by a removable barrier. Removal of the barrier may allow the two parts to be mixed, so that they may form an ophthalmically acceptable liquid. This may allow the ophthalmically acceptable liquid to have a long enough shelf-life.

The removable barrier may have any of a variety of structural features as long as it can separate a stabilizing composition from a liquid vehicle composition and be removed so as to allow mixing of the two compositions. For example, the removable barrier may be two separate containers for the two compositions having removable openings such as caps or lids. Alternatively, the removable barrier may be a feature of a single container having two compartments separated by the removable barrier. Removal of the barrier may damage or destroy the barrier so that it may not be used again. Alternatively, the removable barrier may be reusable.

Some advantages of these ophthalmic pharmaceutical products may include: longer product shelf life, reduced degradation of the therapeutically active agent, lower levels of degradants in product, and/or improved safety and/or tolerability of the product.

A stabilizing composition comprises a therapeutically active agent and other components that may increase stability or are compatible with storage of the therapeutically active agent, such as a solubilizer or dispersing agent, an osmolality agent, a buffer, a preservative, a diluent or bulking agent, and the like. Alternatively, a stabilizing composition may be a solid, containing the therapeutically active agent substantially alone.

The solid may be prepared by lyophilization, blending, milling, granulation or other pharmaceutical processing.

A stabilizing composition may also be a liquid, which contains the therapeutically active agent in solution or suspension in an appropriate stabilizing vehicle. A stabilizing vehicle may be aqueous or non-aqueous, with appropriate stabilizers or excipients included as appropriate. In some embodiments, a liquid stabilizing composition may comprise a solubilizer or dispersing agent, a stabilizer, a buffer, a vehicle, etc.

Any therapeutically active agent may be used in the stabilizing composition. In some embodiments, the therapeutically active agent is unstable to the extent that it cannot be stored for a sufficient time, such as for at least about 3 months, at least about 6 months, or at least about 1 year, in an ophthalmically acceptable liquid. Some non-limiting examples of the therapeutically active agent may include: Phentolamine, Compound 1, Compound 2, DHA, EPA, ALA, cyclosporine, ketorolac, testosterone or a derivative thereof, or pharmaceutically acceptable salts thereof.

Compound 1

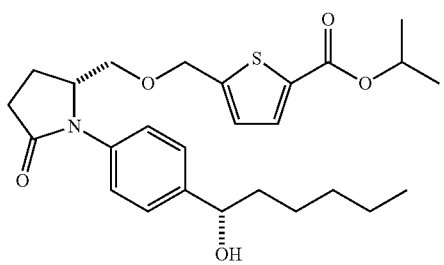

-continued

Compound 2

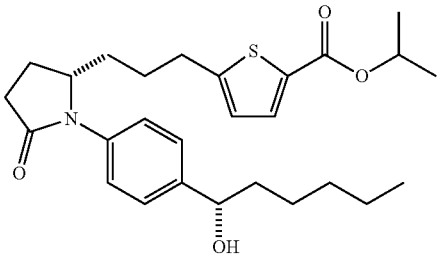

Omega-3 Oil

Flax seed oil, also known as linseed oil, is a clear to yellowish oil obtained from the dried ripe seeds of the flax plant (*Linum usitatissimum*, Linaceae).
Fatty acid components of flaxseed oils:
  57% alpha-linolenic acid (or ALA) all-cis-9,12,15-octadecatrienoic acid, (18:3n–3).

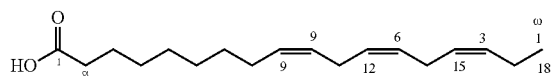

16% Linoleic acid cis,cis,-9,12-octadecadienoic acid, (18:2n–6)

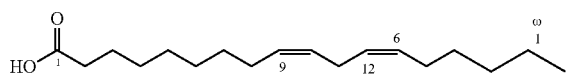

18% Monosaturated fatty acid
9% Saturated fatty acid

EPA vs DHA

ALA is the precursor for the long-chain PUFA (EPA and DHA)

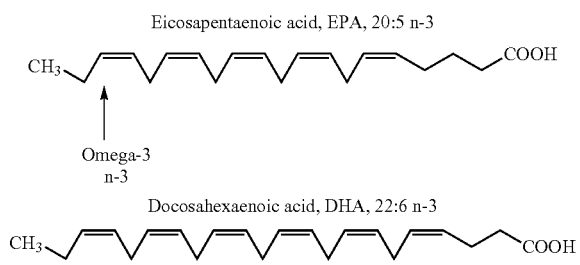

A solubilizer or a dispersing agent may be any compound or substance that can help to solubilize or disperse a therapeutically active agent or another dispersant in a liquid. If a surfactant is used, the surfactant used may vary, and may include any compound or salt that is surface active or can form micelles. A surfactant may be used for assisting in dissolving an excipient or an active agent, dispersing a solid or liquid in a composition, enhancing wetting, modifying drop size, stabilizing an emulsion, or a number of other purposes. Useful surfactants include, but are not limited to, surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal & vegetable); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives. In some embodiments, the surfactant may include polyethylene glycol (15)-hydroxystearate (CAS Number 70142-34-6, available as SOLUTOL HS 15® from BASF), polyoxyethylene-polyoxypropylene block copolymer (CAS No. 9003-11-6, available as PLURONIC® F-68 from BASF), polyoxyethylene 40 stearate (POE40 stearate), polysorbate 80 or polyoxyethylene (80) sorbitan monooleate (CAS No. 9005-65-6), sorbitan monostearate (CAS No. 1338-41-6, available as SPAN™ 60 from Croda International PLC), polyoxyethylenglyceroltriricinoleate 35 (CAS No. 61791-12-6, available as CREMOPHOR EL® from BASF). The amount of surfactant may vary. In some embodiments, the amount of any surfactant such as those listed above may be about 0.001% to about 5%, about 0.1% to about 2%, or about 0.1% to about 1%.

In some embodiments, the solubilizer or dispersing agent may comprise: polyethylene glycol (15)-hydroxystearate, polyoxyethylene-polyoxypropylene block copolymer, polyoxyethylene 40 stearate, polysorbate, sorbitane, polyoxyethylenglyceroltriricinoleate 35, or a cyclodextrin.

Other solubilizing or dispersing agents may be used that are not surface active, but may be useful in solubilizing or dispersing a solid without substantial surface activity. Some non-limiting examples of other solubilizing or dispersing agents that may have minimal surface activity include cyclodextrins, polyvinyl alcohol, povidone, hydroxypropyl methyl cellulose, poloxamers, carboxymethyl cellulose, hydroxyethyl cellulose, acrylates (e.g. PEMULEN®), etc. In some embodiments, the amount of a solubilizing or dispersing agent without substantial surface activity may be about 0.001% to about 20%.

The osmolality agent may vary, and may include any compound or substance useful for adjusting the osmolality of an ophthalmic liquid. Examples include, but are not limited to, salts, particularly sodium chloride or potassium chloride, mannitol glycerin, etc. The amount of osmolality agent may vary depending upon whether an isosmotic, hyperosmotic, or a hyposmotic liquid is desired. In some embodiments, the amount of an osmolality agent such as those listed above may be at least about 0.0001% up to about 1%, about 2%, or about 5%.

The buffer may vary, and may include any weak conjugate acid-base pair suitable for maintaining a desirable pH range. Examples include, but are not limited to, acetate buffers, citrate buffers, phosphate buffers, borate buffers, lactate buffers, NaOH trolamine buffers, or a combination thereof. Acids or bases may be used to adjust the pH of these formulations as needed. The amount of buffer used may vary. In some embodiments, the amount of buffer used may be sufficient so that the buffer has a concentration in a range of about 1 nM to about 100 mM in the ophthalmically acceptable liquid.

The preservative may vary, and may include any compound or substance suitable for prevent microbial contamination in an ophthalmic liquid subject to multiple uses from the same container. Preservatives that may be used in the pharmaceutical compositions disclosed herein include, but are not limited to, cationic preservatives such as quaternary ammonium compounds including benzalkonium chloride, polyquad, and the like; guanidine-based preservatives including PHMB, chlorhexidine, and the like; chlorobutanol; mercury preservatives such as thimerosal, phenylmercuric acetate and phenylmercuric nitrate; and oxidizing preservatives such as stabilized oxychloro complexes (e.g. PURITE® for liquid stabilizing compositions). Combinations of preservatives are also included such as of benzalkonium ion and an oxy-chlorite moiety wherein the benzalkonium ion is benzalkonium chloride and the oxy-chlorite moiety is Purite®. Other preservatives include polyhexamethylene biguanide alone and in combination with benzalkonium chloride and Purite®.

The diluent or bulking agent may vary, and may include any compound or substance to add bulk to a stabilizing composition for ease of handling, or for adjusting a solid stabilizing composition so that it has a desirable solid properties for handling. Non-limiting examples may include mannitol, lactose, trehalose, and the like.

For liquid stabilizing compositions, a vehicle may be used. The vehicle may be any compound or substance that can dissolve or disperse any solids in a stabilizing composition so that the stabilizing composition is in a liquid form or comprises a solid dispersed in a liquid. Some non-limiting examples of vehicles may include silicones, oils, or water. Suitable oils include, but are not limited to anise oil, castor oil, clove oil, cassia oil, cinnamon oil, almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalyptus oil, sesame oil, and the like.

A stabilizer may include any compound that is useful in stabilizing a composition, such as an antioxidant or a chelating/complexing agent.

If the stabilizer includes an antioxidant, the antioxidant may vary, and may include any compound or substance that is useful in reducing oxidation of any compound present in an ophthalmically acceptable liquid. Examples, but are not limited to, ascorbic acid, sodium metabisulfite, sodium thiosulfate, acetylcysteine, butylated hydroxyanisole, and butylated hydroxytoluene.

If the stabilizer includes a chelating/complexing agent, the chelating/complexing agent may vary, and may include any compound or substance that is capable of chelating or complexing a metal or another chemical species. Examples may include, but are not limited to, edetate disodium (EDTA), citrate, phosphate, malonate, maleate, acetate, edetate, ethanol diglycinate, diethanolglycinate, polystyrene sulfonate, etc.

In some embodiments, a stabilizing composition comprises polyethylene glycol (15)-hydroxystearate, polyoxyethylene-polyoxypropylene block copolymer, polyoxyethylene 40 stearate, polysorbate 80, sorbitan monostearate, polyoxyethylenglyceroltriricinoleate 35, a cyclodextrin, or a combination thereof.

In some embodiments, a stabilizing composition comprises potassium chloride, mannitol, sodium chloride, or a combination thereof.

In some embodiments, a stabilizing composition comprises a phosphate buffer, a phosphate citrate buffer, NaOH trolamine, a lactate buffer, a borate buffer, a borate citrate buffer, or a combination thereof.

In some embodiments, a stabilizing composition comprises BAK, Purite, other preservatives or preservative combinations such as combinations of preservatives including benzalkonium ion and an oxy-chlorite moiety wherein the benzalkonium ion is benzalkonium chloride and the oxy-chlorite moiety is Purite®. Other preservatives include polyhexamethylene biguanide alone and in combination with benzalkonium chloride and Purite®.

In some embodiments, the stabilized composition is non-preserved.

In some embodiments, a stabilizing composition comprises mannitol, lactose, trehalose, or a combination thereof.

In some embodiments, a stabilizing composition comprises sodium metabisulfite, ascorbic acid, EDTA, a complexing agent, or a combination thereof.

In some embodiments, a stabilizing composition is an aqueous liquid that may have a pH of about 1 to about 13.

In some embodiments, a stabilizing composition is a solid comprising phentolamine or a salt thereof in an amount of about 0.001% wt/wt to about 10% wt/wt and polyethylene glycol (15)-hydroxystearate in amount of about 0.001% wt/wt to about 5% wt/wt.

In some embodiments, a stabilizing composition is a solid comprising phentolamine or a salt thereof in an amount of about 0.001% wt/wt to about 10% wt/wt and polyoxyethylene-polyoxypropylene block copolymer in amount of about 0.001% wt/wt to about 5% wt/wt.

In some embodiments, a stabilizing composition is a solid comprising phentolamine or a salt thereof in an amount of about 0.001% wt/wt to about 10% wt/wt and polyoxyethylene 40 stearate in amount of about 0.001% wt/wt to about 1% wt/wt.

In some embodiments, a stabilizing composition is a solid comprising phentolamine or a salt thereof in an amount of about 0.001% wt/wt to about 10% wt/wt and polyoxyethylenglyceroltriricinoleate 35 in amount of about 0.001% wt/wt to about 1% wt/wt.

In some embodiments, a stabilizing composition is a solid comprising phentolamine or a salt thereof in an amount of about 0.001% wt/wt to about 10% wt/wt and a cyclodextrin in amount of about 0.001% wt/wt to about 20% wt/wt.

Some embodiments of solid stabilizing compositions are listed in Tables 1 and 2.

TABLE 1

Examples of stabilizing composition as therapeutically active agent alone in powder form

| Ingredient type | Ingredient | Examples of typical conc. range % (w/w) Any one of the below drug substances |
|---|---|---|
| Therapeutically active agent At least one of the drug substances listed | Phentolamine and its salts | 100% |
| | Cyclosporine | 100% |
| | Testosterone, and its derivatives | 100% |
| | Ketorolac, and its salts | 100% |
| | DHA, and its salts | 100% |
| | EPA, and its salts | 100% |
| | ALA, and its salts | 100% |

TABLE 2

Examples of stabilizing compositions as therapeutically active agent with other excipients powder form

| Ingredient type | Ingredient | Examples of typical conc. range % (w/w) Any one of the below drug substances |
|---|---|---|
| Therapeutically active agent At least one of the drug substances listed and mixtures thereof are contemplated | Phentolamine and its salts | about 0.001-10% |
| | Cyclosporine | about 0.001-10% |
| | Testosterone, and its derivatives | about 0.001-10% |
| | Ketorolac, and its salts | about 0.001-10% |
| | DHA, and its salts | about 0.001-10% |
| | EPA, and its salts | about 0.001-10% |
| | ALA, and its salts | about 0.001-10% |
| | COMPOUND 1 | about 0.001-10% |
| | COMPOUND 2 | about 0.0002-10% |
| Following ingredients may or may not be included in the formulation Part 1 | | |
| Solubilizer/ dispersing agents (may or may not be required) | Solutol HS 15 | about 0.001-5% |
| | Pluronic F68 | about 0-5% |
| | POE40Stearate | about 0-1% |
| | Cyclodextrins | about 0-10% |
| Osmolality agents (any one or two or more in combinations) | Potassium chloride | about 0-2% |
| | Mannitol | about 0-5% |
| | Sodium chloride | about 0-1% |
| Buffers (Any one of the buffers listed) | Phosphate buffer | *q.s. for about 1-100 mM |
| | Phosphate citrate buffer | *q.s. for about 1-100 mM |
| | NaOH/ Trolamine | *q.s. for about 1-100 mM |
| | Lactate buffer | *q.s. for about 1-100 mM |
| | Borate buffer | *q.s. for about 1-100 mM |
| | Borate citrate | *q.s. for about 1-100 mM |
| Water soluble Antioxidants | EDTA | 0-1% |
| | Pyruvate | 0-1% |
| | Trehalose | 0-10% |
| Oil Soluble Antioxidants | Alpha-Tocopherol Ascorbyl Palmitate BHA BHT | 0-1% |
| Preservatives (Any one or in combination) | None - Non preserved | NA |
| | BAK | *q.s. for about 10-200 ppm |
| | Purite | 20-150 ppm |
| | BAK + Purite combo | 0.1 to 2000 ppm of Purite and from 1 to 100 ppm of benzalkonium ion |
| | PHMB + BAK combo | 0.1 to 10 ppm PHMB and 0.1 to 30 ppm benzalkonium ion. |
| Diluent/bulking agent/ cake formers | Mannitol | q.s. to 100% |
| | Lactose | q.s. to 100% |
| | Trehalose | q.s. to 100% |

*q.s to achieve listed concentration in final formulation after reconstitution

In some embodiments, a stabilizing composition includes a therapeutically active agent listed in Table 2 and a solubilizer/dispersing agent listed in Table 2.

In some embodiments, a stabilizing composition includes a therapeutically active agent listed in Table 2 and an osmolality agent listed in Table 2.

In some embodiments, a stabilizing composition includes a therapeutically active agent listed in Table 2 and a buffer listed in Table 2.

In some embodiments, a stabilizing composition includes a therapeutically active agent listed in Table 2 and a preservative listed in Table 2.

In some embodiments, a stabilizing composition includes a therapeutically active agent listed in Table 2 and a diluent listed in Table 2.

In some embodiments, a stabilizing composition includes a therapeutically active agent listed in Table 2, a solubilizer/dispersing agent listed in Table 2, and a osmolality agent listed in Table 2.

In some embodiments, a stabilizing composition includes a therapeutically active agent listed in Table 2, a solubilizer/dispersing agent listed in Table 2, and a buffer listed in Table 2.

In some embodiments, a stabilizing composition includes a therapeutically active agent listed in Table 2, a solubilizer/dispersing agent listed in Table 2, and a preservative listed in Table 2.

In some embodiments, a stabilizing composition includes a therapeutically active agent listed in Table 2, a solubilizer/dispersing agent listed in Table 2, and a diluent listed in Table 2.

In some embodiments, a stabilizing composition includes a therapeutically active agent listed in Table 2, an osmolality agent listed in Table 2, and a buffer listed in Table 2.

In some embodiments, a stabilizing composition includes a therapeutically active agent listed in Table 2, an osmolality agent listed in Table 2, and a preservative listed in Table 2.

In some embodiments, a stabilizing composition includes a therapeutically active agent listed in Table 2, an osmolality agent listed in Table 2, and a diluent listed in Table 2.

In some embodiments, a stabilizing composition includes a therapeutically active agent listed in Table 2, a buffer listed in Table 2, and a preservative listed in Table 2.

In some embodiments, a stabilizing composition includes a therapeutically active agent listed in Table 2, a buffer listed in Table 2, and a diluent listed in Table 2.

In some embodiments, a stabilizing composition includes a therapeutically active agent listed in Table 2, a preservative listed in Table 2, and a diluent listed in Table 2.

In some embodiments, a stabilizing composition includes a therapeutically active agent listed in Table 2, a solubilizer/dispersing agent listed in Table 2, a osmolality agent listed in Table 2, and a buffer listed in Table 2.

In some embodiments, a stabilizing composition includes a therapeutically active agent listed in Table 2, a solubilizer/dispersing agent listed in Table 2, a osmolality agent listed in Table 2, and a preservative listed in Table 2.

In some embodiments, a stabilizing composition includes a therapeutically active agent listed in Table 2, a solubilizer/dispersing agent listed in Table 2, a osmolality agent listed in Table 2, and a diluent listed in Table 2.

In some embodiments, a stabilizing composition includes a therapeutically active agent listed in Table 2, a solubilizer/dispersing agent listed in Table 2, a buffer listed in Table 2, and a preservative listed in Table 2.

In some embodiments, a stabilizing composition includes a therapeutically active agent listed in Table 2, a solubilizer/dispersing agent listed in Table 2, a buffer listed in Table 2, and a diluent listed in Table 2.

In some embodiments, a stabilizing composition includes a therapeutically active agent listed in Table 2, a solubilizer/dispersing agent listed in Table 2, a preservative listed in Table 2, and a diluent listed in Table 2.

In some embodiments, a stabilizing composition includes a therapeutically active agent listed in Table 2, an osmolality agent listed in Table 2, a buffer listed in Table 2, and a preservative listed in Table 2.

In some embodiments, a stabilizing composition includes a therapeutically active agent listed in Table 2, an osmolality agent listed in Table 2, a buffer listed in Table 2, and a diluent listed in Table 2.

In some embodiments, a stabilizing composition includes a therapeutically active agent listed in Table 2, an osmolality agent listed in Table 2, a preservative listed in Table 2, and a diluent listed in Table 2.

In some embodiments, a stabilizing composition includes a therapeutically active agent listed in Table 2, a buffer listed in Table 2, a preservative listed in Table 2, and a diluent listed in Table 2.

Some embodiments of liquid stabilizing compositions are listed in Table 3.

TABLE 3

Examples of stabilizing compositions as liquid containing therapeutically active agent

| Ingredient type | Ingredient | Examples of typical conc. range % (w/w) |
|---|---|---|
| Active Ingredients Any one of the drug substances listed | Phentolamine and its salts | Any one of the below drug substances about 0.001-10% |
| | Cyclosporine | about 0.001-10% |
| | Testosterone, and its derivatives | about 0.001-10% |
| | Ketorolac, and its salts | about 0.001-10% |
| | COMPOUND 1 | about 0.001-10% |
| | COMPOUND 2 | about 0.0002-10% |
| Following ingredients may or may not be included in the formulation Part 1 | | |
| Solubilizer/ Co-solubilizer/dispersing agents (may or may not be required) | Solutol HS 15 | about 0-10% |
| | Polysorbate 80 | about 0-10% |
| | Span 60 | about 0-10% |
| | Pluronic F68 | about 0-10% |
| | POE40Stearate | about 0-10% |
| | Cremophor EL | about 0-10% |
| | Cyclodextrins | about 0-20% |
| Stabilizers (may or may not be required) | Sodium Metabisulfate | about 0-1% |
| | Ascorbic acid | about 0-1% |
| | EDTA | about 0-1% |
| | Complexing agents | about 0-40% |
| Buffers (may or may not be required) | Phosphate buffer | about 0-100 mM |
| | Phosphate citrate buffer | about 0-100 mM |
| | NaOH/ Trolamine | about 0-100 mM |
| | Lactate buffer | about 0-100 mM |
| | Borate buffer | about 0-100 mM |
| | Borate citrate | about 0-100 mM |
| | NaOH or HCl for pH adjustment | Q.S |
| pH range | (for aqueous formulations) | pH 1 to 13 |
| Vehicle | Silicones | QS |
| | Oil | QS |
| | Water | QS |

In some embodiments, the stabilizing composition includes a therapeutically active agent listed in Table 3 and a solubilizer/dispersing agent listed in Table 3.

In some embodiments, the stabilizing composition includes a therapeutically active agent listed in Table 3 and a stabilizer listed in Table 3.

In some embodiments, the stabilizing composition includes a therapeutically active agent listed in Table 3 and a buffer listed in Table 3.

In some embodiments, the stabilizing composition includes a therapeutically active agent listed in Table 3, a solubilizer/dispersing agent listed in Table 3 and a stabilizer listed in Table 3.

In some embodiments, the stabilizing composition includes a therapeutically active agent listed in Table 3, a solubilizer/dispersing agent listed in Table 3, and a buffer listed in Table 3.

In some embodiments, the stabilizing composition includes a therapeutically active agent listed in Table 3, a stabilizer listed in Table 3, and a buffer listed in Table 3.

In some embodiments, the stabilizing composition includes a therapeutically active agent listed in Table 3, a solubilizer/dispersing agent listed in Table 3, a stabilizer listed in Table 3, and a buffer listed in Table 3.

A liquid vehicle composition may be any liquid comprising a silicone or water that may be mixed with a stabilizing composition to provide a sterile ophthalmically acceptable liquid. An ophthalmically acceptable liquid includes a liquid that is tolerable to a patient for topical ophthalmic use. A liquid vehicle composition may also comprise any of a solubilizer or dispersing agent, a stabilizer, a buffer, and/or a preservative, as described above. Furthermore, a liquid vehicle composition may have a pH in the range of about 5 to about 8.

The relative amounts of a stabilizing composition and a liquid vehicle composition may vary. In some embodiments a stabilizing composition may be about 0.001% to about 10%, or about 0.01% to about 10% of the ophthalmically acceptable liquid.

In some embodiments, a liquid vehicle composition comprises polyethylene glycol (15)-hydroxystearate, polyoxyethylene-polyoxypropylene block copolymer, polyoxyethylene 40 stearate, polysorbate 80, sorbitan monostearate, polyoxyethylenglyceroltriricinoleate 35, a cyclodextrin, or a combination thereof.

In some embodiments, a liquid vehicle composition comprises sodium metabisulfite, ascorbic acid, EDTA, a complexing agent, or a combination thereof.

In some embodiments, a liquid vehicle composition comprises a phosphate buffer, a phosphate citrate buffer, a NaOH/trolamine buffer, a lactate buffer, a borate buffer, a borate citrate buffer, or a combination thereof.

In some embodiments, a liquid vehicle composition is non-preserved, or comprises benzalkonium chloride or a stabilized oxychloro complex.

In some embodiments, a liquid vehicle composition is an aqueous liquid with a pH of about 5 to about 8.

In some embodiments, a liquid vehicle composition comprises a silicone.

TABLE 4

Examples of liquid vehicle compositions

| Ingredient type | Ingredient | Examples of typical conc. range % (w/w) |
|---|---|---|
| Following ingredients may or may not be included in the formulation Part 2 | | |
| Solubilizer/ Co-solubilizer/dispersing agents (may or may not be required) | Solutol HS 15 | about 0-10% |
| | Polysorbate 80 | about 0-10% |
| | Span 60 | about 0-10% |
| | Pluronic F68 | about 0-10% |
| | POE40Stearate | about 0-10% |
| | Cremophor EL | about 0-10% |
| | Cyclodextrins | about 0-20% |
| Stabilizers (may or may not be required) | Sodium Metabisulfate | about 0-1% |
| | Ascorbic acid | about 0-1% |
| | EDTA | about 0-1% |
| | Complexing agents | about 0-40% |
| Buffers (may or may not be required) | Phosphate buffer | about 0-100 mM |
| | Phosphate citrate buffer | about 0-100 mM |
| | NaOH/ Trolamine | about 0-100 mM |
| | Lactate buffer | about 0-100 mM |
| | Borate buffer | about 0-100 mM |
| | Borate citrate | about 0-100 mM |

TABLE 4-continued

Examples of liquid vehicle compositions

| Ingredient type | Ingredient | Examples of typical conc. range % (w/w) |
|---|---|---|
| | Following ingredients may or may not be included in the formulation Part 2 | |
| | NaOH or HCl for pH adjustment | Q.S |
| Preservatives and combinations | None - Non preserved | NA |
| | BAK | about 10-200 ppm |
| | Purite | about 10-300 ppm |
| Vehicle (one of these required) | Silicones (non-aqueous formulas) | QS |
| | Water (aqueous formulas) | QS |
| pH range | (for aqueous formulations) | pH about 5 to 8 |

In some embodiments, a liquid vehicle composition comprises a solubilizer/dispersing agent listed in Table 4.

In some embodiments, a liquid vehicle composition comprises a stabilizer listed in Table 4.

In some embodiments, a liquid vehicle composition comprises a buffer listed in Table 4.

In some embodiments, a liquid vehicle composition comprises a preservative listed in Table 4.

In some embodiments, a liquid vehicle composition comprises a solubilizer/dispersing agent listed in Table 4 and a stabilizer listed in Table 4.

In some embodiments, a liquid vehicle composition comprises a solubilizer/dispersing agent listed in Table 4 and a buffer listed in Table 4.

In some embodiments, a liquid vehicle composition comprises a solubilizer/dispersing agent listed in Table 4 and a preservative listed in Table 4.

In some embodiments, a liquid vehicle composition comprises a stabilizer listed in Table 4 and a buffer listed in Table 4.

In some embodiments, a liquid vehicle composition comprises a stabilizer listed in Table 4 and a preservative listed in Table 4.

In some embodiments, a liquid vehicle composition comprises a buffer listed in Table 4 and a preservative listed in Table 4.

In some embodiments, a liquid vehicle composition comprises a solubilizer/dispersing agent listed in Table 4, a stabilizer listed in Table 4, and a buffer listed in Table 4.

In some embodiments, a liquid vehicle composition comprises a solubilizer/dispersing agent listed in Table 4, a stabilizer listed in Table 4, and a preservative listed in Table 4.

In some embodiments, a liquid vehicle composition comprises a solubilizer/dispersing agent listed in Table 4, a buffer listed in Table 4, and a preservative listed in Table 4.

In some embodiments, a liquid vehicle composition comprises a stabilizer listed in Table 4, a buffer listed in Table 4, and a preservative listed in Table 4.

In some embodiments, a liquid vehicle composition comprises a solubilizer/dispersing agent listed in Table 4, a stabilizer listed in Table 4, a buffer listed in Table 4, and a preservative listed in Table 4.

Example 1

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. An ophthalmic pharmaceutical product comprising:
  a stabilizing composition comprising a therapeutically active agent;
  a liquid vehicle composition;

a removable barrier;
wherein the removable barrier is in simultaneous contact with the stabilizing composition and the liquid composition and the removable barrier is configured to prevent contact between the stabilizing composition and the liquid vehicle composition; and
wherein the product is configured to allow removal of the barrier;
wherein the product is configured so that removal of the barrier allows mixing of the stabilizing composition and the vehicle composition to provide a sterile ophthalmically acceptable liquid; and
wherein the ophthalmically acceptable liquid comprises a therapeutic amount of the therapeutically active agent; and
wherein the therapeutically active agent is selected from the group consisting of phentolamine, cyclosporin, ketorolac, testosterone or a derivative thereof, docosehexaenoic acid, eicosapentaenoic acid, alpha-linolenic acid,

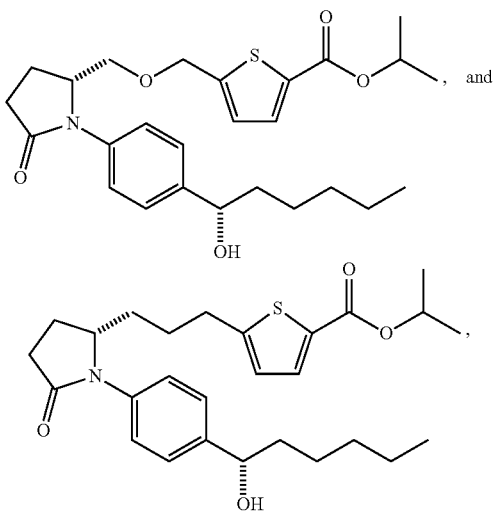
, and or a pharmaceutically acceptable salt thereof.

2. The product of claim 1, wherein the therapeutically active agent is phentolamine or a salt thereof.

3. The product of claim 1, wherein the therapeutically active agent is a cyclosporine.

4. The product of claim 1, wherein the therapeutically active agent is testosterone or a derivative thereof.

5. The product of claim 1, wherein the therapeutically active agent is:

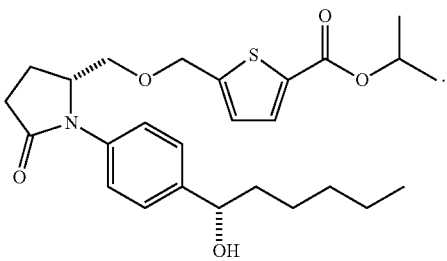 [SMILES: CCCCC[C@H](O)c1ccc(N2C(=O)CC[C@@H]2COCc2ccc(C(=O)OC(C)C)s2)cc1]

6. The product of claim 1, wherein the therapeutically active agent is:

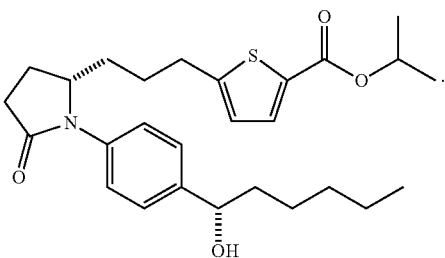 [SMILES: CCCCC[C@H](O)c1ccc(N2C(=O)CC[C@@H]2CCCc2ccc(C(=O)OC(C)C)s2)cc1]

7. The product of claim 1, wherein the stabilizing composition comprises polyethylene glycol (15)-hydroxystearate, polyoxyethylene-polyoxypropylene block copolymer, polyoxyethylene 40 stearate, polysorbate 80, sorbitan monostearate, polyoxyethylenglyceroltriricinoleate 35, a cyclodextrin, or a combination thereof.

8. The product of claim 1, wherein the stabilizing composition comprises potassium chloride, mannitol, sodium chloride, or a combination thereof.

9. The product of claim 1, wherein the stabilizing composition comprises a phosphate buffer, a phosphate citrate buffer, NaOH trolamine, a lactate buffer, a borate buffer, a borate citrate buffer, or a combination thereof.

10. The product of claim 1, wherein the stabilizing composition comprises benzalkonium chloride or is non-preserved.

11. The product of claim 1, wherein the stabilizing composition comprises mannitol, lactose, trehalose, or a combination thereof.

12. The product of claim 1, wherein the liquid vehicle composition comprises polyethylene glycol (15)-hydroxystearate, polyoxyethylene-polyoxypropylene block copolymer, polyoxyethylene 40 stearate, polysorbate 80, polyoxyethylenglycerol triricinoleate 35, a cyclodextrin, or a combination thereof.

13. The product of claim 1, wherein the liquid vehicle composition comprises polyethylene glycol (15)-hydroxystearate, polyoxyethylene-polyoxypropylene block copolymer, polyoxyethylene 40 stearate, polysorbate 80, sorbitan monostearate, polyoxyethylenglyceroltriricinoleate 35, a cyclodextrin, or a combination thereof.

14. The product of claim 1, wherein the liquid vehicle composition is non-preserved, or comprises benzalkonium chloride or a stabilized oxychloro complex.

15. The product of claim 1, wherein the liquid vehicle composition is an aqueous liquid with a pH of about 5 to about 8.

16. A method of stabilizing a therapeutically active agent for use in an ophthalmically acceptable liquid comprising:
providing a stabilizing system comprising:
a stabilizing composition comprising the therapeutically active agent;
a vehicle composition comprising at least one of: a solubilizer, a surfactant, an osmolality agent, a buffer, and a preservative; and
a removable barrier separating the stabilizing composition from the vehicle composition;
wherein the system is configured so that removal of the barrier allows mixing between the stabilizing composition and the vehicle to provide a sterile ophthalmically acceptable liquid; and
wherein the ophthalmically acceptable liquid comprises about 0.0001% to about 5% therapeutically active agent by weight and wherein the therapeutically active agent is selected from the group consisting of phentolamine, cyclosporin, ketorolac, testosterone or a derivative thereof, docosehexaenoic acid, eicosapentaenoic acid, alpha-linolenic acid,

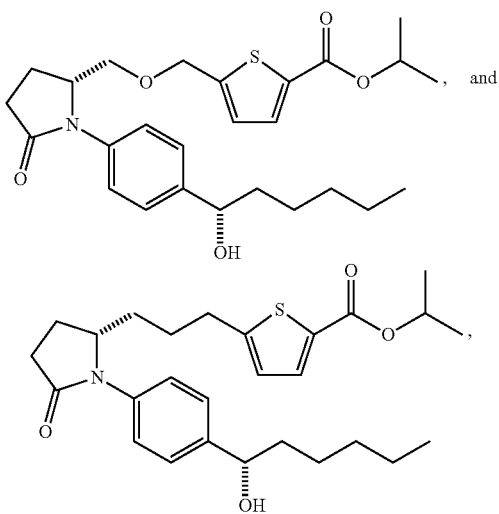

, and or a pharmaceutically acceptable salt thereof.

17. The method of claim 16, wherein the therapeutically active agent is phentolamine or a salt thereof.

18. The method of claim 16, wherein the therapeutically active agent is a cyclosporine.

19. The method of claim 16, wherein the therapeutically active agent is:

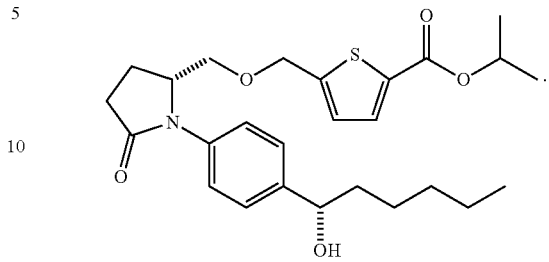

20. The method of claim 16, wherein the therapeutically active agent is:

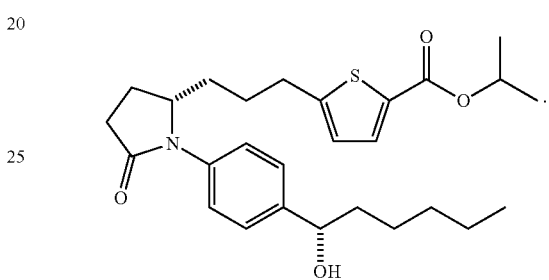

* * * * *